United States Patent [19]
Bento et al.

[11] Patent Number: 5,250,182
[45] Date of Patent: Oct. 5, 1993

[54] MEMBRANE-BASED PROCESS FOR THE RECOVERY OF LACTIC ACID AND GLYCEROL FROM A "CORN THIN STILLAGE" STREAM

[75] Inventors: John M. A. Bento, Downsville, Canada; Hubert L. Fleming, Sussex, N.J.

[73] Assignee: Zenon Environmental Inc., Burlington, Canada

[21] Appl. No.: 912,320

[22] Filed: Jul. 13, 1992

[51] Int. Cl.$^5$ .............................................. B01D 61/58
[52] U.S. Cl. ..................................... 210/641; 210/651; 210/259
[58] Field of Search ............... 210/641, 651, 652, 259; 426/656

[56] References Cited

U.S. PATENT DOCUMENTS 4,624,805  11/1986  Lawhon ........................... 426/656 X

OTHER PUBLICATIONS

"Ultrafiltration & Reverse Osmosis Technology & Alcohol Applications" by Craig Brandon, Bill McFadden and Rodney L. Simms presented at 1991 Fuel Alcohol Workshop.

"Nanofiltration Extends the Range of Membrane Filtration" by Peter Eriksson Environmental Progress vol. 7, No. 1 pp. 58-62 Feb. 1988.

"Reverse Osmosis of Lactic Acid Fermentation Broths" by Laura R. Schlicher & Munir Cheryan, J. Chem. Tech. Biotechnol 02 vol. 49, pp. 129-140 1990.

"Cross-Flow Ceramic Membrane Microfiltration for the Clarification of Ethanol Stillbottoms" by Brian D. Burris presented to Intnl. Conf. on (Fuel) Alcohols etc.

"Membrance Process Designs in the Recovery of Bio-Fuels and Bio-Chemicals" by S. A. Leeper Idaho National Engineering Laboratory, Idaho Falls, ID. 83415.

*Primary Examiner*—Frank Spear
*Attorney, Agent, or Firm*—Alfred D. Lobo

[57] ABSTRACT

"Thin stillage", discharged from a centrifuge in which relatively large $>10$ μm insoluble solids in an ethanol stillbottoms stream are separated from "whole stillage", is separated in a step-wise membrane separation process to recover lactic acid and glycerol, together. In each step, the permeate recovery is at least 50%. In a first step, an ultrafiltration (UF) membrane means produces a UF permeate stream in which not only essentially all the insoluble portion of said thin stillage $>0.0.05$ μm is removed as UF concentrate, but also at least 50% of solubles having a molecular weight $>2\times10^5$ Daltons, including dissolved proteins in said thin stillage. In a second step to which the UF permeate is fed, a nanofiltration (NF) membrane produces a NF permeate with a rejection of less than 30% of both the lactic acid and the glycerol, preferably less than 25%. Essentially all molecules larger than lactic acid or glycerol are removed in the NF concentrate. In a third step, to which the NF permeate is fed, a reverse osmosis (RO) membrane means produces demineralized RO water which contains essentially no lactic acid and glycerol, because these are rejected in the RO concentrate. Use of the membrane separation process in the production of ethanol based on the dry-milling of corn, eliminates the use of a conventional evaporator.

12 Claims, 3 Drawing Sheets

MEMBRANE-BASED PROCESS FOR THE RECOVERY OF LACTIC ACID AND GLYCEROL FROM A "CORN THIN STILLAGE" STREAM

BACKGROUND OF THE INVENTION

The production of ethanol by a process based on the "dry milling of corn", comprises enzymatically converting starch in the corn to sugar, then fermenting the sugar to produce a "beer" from which industrial grade ethanol is recovered by distilling the beer. This fermentation process produces, along with the ethanol product, a small quantity of lactic acid (2-hydroxypropanoic acid) and glycerol (1,2,3-propanetriol) as by-products. To date, the solids recovered from the beer are the major by-product which is sold as DDG (distillers dried grain) or DDGS (distillers dried grain solubles). Ethanol production using the dry milling process also generates several other by-products none of which is recovered either individually, or one with another, in combination, because they are produced in too low a concentration (hereafter "conc" for brevity) to make recovery economical. With specific respect to lactic acid and glycerol, to date, the perceived wisdom of running an ethanol plant using the dry milling process required minimizing the formation of glycerol and lactic acid, because the lactic acid in particular, suppressed the formation of ethanol and adversely affected profitability. Moreover formation of lactic acid and glycerol consumes valuable substrate (or fermentable sugars).

Since the economics of increasing ethanol at the expense of depressing the concentrations of lactic acid and glycerol formed, were not inviting, it was decided to separate the lactic acid and glycerol. This process is directed to the recovery of both lactic acid and glycerol, together, from a stream of aqueous solids ("whole stillage") produced from the bottoms of an ethanol fractionation column such as is conventionally used in a corn dry-milling ethanol plant.

More specifically this invention relates to the recovery of both lactic acid and glycerol, together, from "corn thin stillage" (or, "thin stillage" for brevity) discharged from a centrifuge in which relatively large, water-insoluble, solids in the "whole stillage" are separated. In a conventional ethanol plant for the dry-milling process, centrifugally separated solids from the whole stillage are fed to rotary driers where the solids are mixed with syrup produced in evaporators (see flow sheet of conventional plant, FIG. 1) and dried to produce DDG or DDGS. The operation and maintenance of the evaporators are to produce the syrup by removing water from the filtered thin stillage stream. This thin stillage typically contains a substantial concentration of water-insoluble ("suspended") solids, as well as "dissolved" solids, generally, only the solids larger than 10 $\mu$m in nominal diameter having been removed. Even with an exceptionally effective centrifuge, only solids larger than 1 $\mu$m may be removed. The solids, both suspended ("insolubles.") and dissolved, foul evaporators, so that their operation and maintenance is a major cost of operating a corn dry milling ethanol plant. Even a slight reduction in the costs of operating and maintaining the evaporators produces a dramatic increase in profitability. The term "insolubles" herein refers to material which is water-insoluble.

Because lactic acid and glycerol are present in the thin stillage in relatively very small amounts, together in a conc less than 5% on a weight basis (weight lactic acid and glycerol/weight thin stillage or "w/w"), recovering them has been such a technically unpromising and predictably unrewarding task, that to date, there has been no attempt, in a commercial process, to do so. Though, on a laboratory scale, the separation of lactic acid and glycerol from thin stillage is not an unusually demanding task, there is no record in the prior art of an operable process with the potential, commercially to recover either lactic acid or glycerol, or both together, from thin stillage.

The reason for the failure to provide an economical process appears to have been a widespread misappraisal and misjudgment of the ability of a membrane means to make a critically important separation in the initial filtration step; and, the failure to realize that the essentially identical relatively low molecular weights of lactic acid and glycerol fortuitously allow their separation and recovery, in combination, from an aqueous stream containing proteins and relatively high mol wt ($C_{10}$–$C_{24}$) fatty acids, provided the "right" membranes are used in the "right" combination.

A study of the use of microfiltration ("MF") or ultrafiltration ("UF") membranes in prior art filtration of thin stillage and "steep water" (obtained in a process for wet milling corn) streams, discloses that the main reason for their use is to remove insolubles. Such insolubles, which are very finely divided solid particles dispersed in thin stillage, were filtered from the thin stillage prior to evaporating it in an evaporator used in the corn dry-milling process. Since the main concern was to reduce fouling of the evaporator by dispersed solids, there was no evident concern as to what "solubles" may be entrained in the filtered thin stillage.

It will be appreciated that the term "evaporator" is used herein specifically to refer to the unit operation of concentrating thin stillage in a conventional evaporator used in a conventional facility for the production of ethanol based on the dry-milling of corn. The function of such evaporator means is separate and distinct from that of "dryers", typically rotary dryers, used to dry a mixture of centrifuged ethanol stillbottoms (solids) and syrup such as is conventionally produced in the evaporators.

In contrast, the process of this invention uses a UF system including at least one UF module in a first filtration step to remove a major portion of soluble proteins along with the insolubles at such a high recovery that the concentrate produced does not have to be flowed to an evaporator. "Recovery" is defined as the percent by volume (vol %) of permeate removed, based on 100 volumes of feed to the UF system during the period it is in operation.

It is critical in this step-wise filtration process that the permeate recovery be at least 50% in each filtration step, most particularly in the first step comprising ultrafiltering the thin stillage. It will be appreciated that the higher the permeate recovery in the first step, the higher the recovery of lactic acid and glycerol in the overall process. More specifically, it will be appreciated that since there is essentially no rejection (less than about 1% for each, lactic acid and glycerol) a permeate recovery of 80% in the first step results in an 80% yield of lactic acid and glycerol. Stated differently, for 100 gallons (gal) of thin stillage containing 1.5% lactic acid, the yield is 80 gal of UF permeate containing 1.5% lactic acid. An equal conc of lactic acid leaves with the UF concentrate.

Further, if 100 gal of UF permeate containing only 1% lactic acid are flowed to the second step, namely nanofiltration ("NF") in the membrane separation process carried out in the membrane means used herein, then if 75 gal of permeate are recovered (75% permeate recovery), and the rejection of lactic acid is 25%, the concentration of lactic acid in the NF permeate is 0.75%.

If in a final step, the reverse osmosis ("RO") step in this invention, the permeate recovery was as high as 90%, then the overall permeate recovery for the process would be the product of the individual permeate recoveries in each separation step. If, as is desirable, the permeate recovery in the UF first step is as high as 80%, in the NF second step is as high as 75%, and in the RO third step is as high as 90%, overall permeate recovery is $0.8 \times 0.75 \times 0.9 = 0.54$.

Since under the most desirable conditions, the overall permeate recovery appeared to be unattractive, there was no motivation to probe the advantages of a process in which the thin stillage was ultrafiltered under particularly specified conditions which provide at least 50% recovery in each step. There was no reason to suspect that such a membrane process would dispense with the conventional use of an evaporator for thin stillage, and, as will be explained hereafter, obviate having to cope with the fouling problems which are the basis for disproportionately large maintenance costs.

In the context of this process it is important to note that the terms MF and UF refer to distinctly different membranes for use in separate and distinct filtration operations, and in the first step of the process of this invention, a MF membrane cannot be used in lieu of a UF membrane. Still other membranes used to make separations in this process are a nanofiltration (NF) membrane and a reverse osmosis (RO) membrane. A MF membrane is used to remove very finely divided solids which are insoluble. The range of sizes of pores in a MF membrane are in the range from 0.2 $\mu$m (micrometers or microns) to 10 $\mu$m. A UF membrane used in the process of this invention necessarily separates particles smaller than 0.2 $\mu$m, preferably in the range from 0.005$\mu$m-0.1 $\mu$m, and, soluble materials based on molecular weight ("mol wt" for brevity), typically in the range from 1000-200,000 Daltons, referred to as "heavies". A nanofiltration ("NF") membrane is semipermeable and non-porous, and provides a further separation based both on mol wt and ionic charge. Molecular weight cut-offs for non-ionized molecules are typically in the range from 150-1000 Daltons, referred to as "lights". For ions of the same mol wt, membrane rejections will increase progressively for ionic charges of 0, 1, 2, 3 etc. for a particular membrane because of increasing charge density (see "Nanofiltration Extends the Range of Membrane Filtration" by Peter Eriksson, *Environmental Progress*, Vol 7, No 1, pp 58-59, February 1988). A RO membrane is also semipermeable and non-porous, and requires an aqueous feed to be pumped to it at a pressure above the osmotic pressure of the dissolved substances in the water. Because an RO membrane can effectively remove low mol wt molecules <150 Daltons, and also ions from water, RO membranes are commonly used to demineralize water (e.g. for pretreating boiler feedwater, and recovering potable water from brackish water or sea water).

The desirability of recovering lactic acid and glycerol essentially free from proteins and relatively high mol wt (>200 Daltons) organic compounds from the by-product stream has been fueled by a long-felt need for cheap lactic acid. There are a multiplicity of uses of lactic acid in the food, drug and related industries. Lately there has been a growing emphasis on the use of polymers of monomers derived from lactic acid because they are biodegradable. Glycerol is used not only as an intermediate in numerous syntheses but also as a copolymer with lactic acid for biodegradable resins, and in the pharmaceutical industry. The process of this invention is directed to help satisfy that long-felt need.

The possibility of recovering lactic acid and glycerol from the by-product stream by filtration was first recognized by Brian Burris in a paper titled "Cross-Flow Ceramic Membrane Microfiltration for the Clarification of Ethanol Stillbottoms" presented to the International Conference On (Fuel) Alcohols and Chemicals from Biomass in Guadaljara, Mexico (Winter 1989). He reported that microfiltered (MF) permeate was "sparkling" clear and contained insolubles of less than 0.08%. He evaporated the clarified MF permeate and reduced the fouling of the evaporator, at the same time reducing the viscosity of the evaporated stream (syrup). He suggested that the lactic acid and glycerol could be recovered from the syrup so obtained by conventional means.

Burris reported that a large scale test had been conducted in a 10 MM gal/yr fuel grade alcohol distillery which used dry-milling. Although this plant, unlike most other distillers, centrifuged their feed solution prior to distillation, they had to shut down every ten days to two weeks because the stillbottoms' evaporator would "scum up" with solids. This company had previously evaluated a spiral wound ultrafilter system which proved ineffective due to plugging. Also evaluated was a tubular polymeric cross-flow filtration unit which produced good clarity product for long periods of time with minimal cleaning.

The term "cross-flow" refers to flow in which there are three streams—feed, permeate and concentrate. In contrast, a "dead end" or "depth" filter has two streams—feed and filtrate (or permeate). In cross-flow feed flow through membrane channels, either parallel (or tangential) to the membrane surface, is separated into a concentrate (and/or recycle) stream and permeate stream. The recycle stream retains all the particles and large molecules rejected by the membrane. The feed/recycle stream mixture flows through filter channels and may be totally recycled to the membrane module, or partially removed form the system as reject (concentrate). The flow of feed parallel to the membrane surface creates shear forces and/or turbulence to sweep away accumulating particles rejected by the membrane (see Burris, supra).

Burris presented data comparing flux versus average transmembrane pressure readings at two cross-flow velocities; and, also presented flux decline data (which was minimal) during 10x concentration. The data were obtained with a 0.5 $\mu$m membrane. Other membranes used were 0.8 $\mu$m and 0.2 $\mu$m. In all cases the thin stillage was only microfiltered so that solids with a nominal diameter <0.2 $\mu$m and 'heavies' remained in the MF permeate. Such small solids were insufficient to vitiate the clarity of the MF permeate and greatly improved the operation of the evaporators. The MF step, introduced to clarify thin stillage before it is flowed to the evaporator, is diagrammatically illustrated in phantom outline in FIG. 1 which depicts an otherwise conventional ethanol recovery process based on the dry-milling of corn.

Since Burris' goal was to minimize the cost of maintaining and operating the evaporator, he was not concerned with removing insolubles smaller than 0.1 μm. Nor was he concerned with removing high mol wt solids above $2 \times 10^5$ Daltons. The purpose for microfiltration was solely to provide sparkling clear, filtered thin stillage for the evaporator. There is no suggestion that the separation of lactic acid and glycerol, from the syrup produced by evaporation of thin stillage, be made by any membrane filtration process.

Therefore there was no motivation to explore the limitations of operating a UF system as a first step for the particular purpose of separating from the thin stillage, not only insolubles $>1$ μm, but also those insolubles $>0.1$ μm along with dissolved solids $>2 \times 10^5$ Daltons.

The total solids concentration (including lactic acid and glycerol) in the thin stillage feed is in the range from 5%–12%, more typically in the range from 6%–10%. This thin stillage is ultrafiltered in the first step of the novel process to provide a permeate recovery high enough to yield a concentrate with a total solids conc in the range from at least 15% to as high as 35%, preferably 20%–30%. The combined concentration of lactic acid and glycerol, typically in the range from 1–3%, depends upon the amount produced in the fermentation process. The minimum yield of lactic acid and glycerol recovered in an economical plant operation is about 40% based on the conc of lactic acid in the thin stillage. The recovery is preferably in the range from about 45–70%, and may be as high as 90% if diafiltration is used. In general, the higher the concentration of lactic acid in the thin stillage, the better the recovery. The same is substantially true for the glycerol. Note that the conc of lactic acid and glycerol in the UF permeate is substantially independent of UF recovery because there is essentially no rejection of either by an appropriately chosen UF membrane.

SUMMARY OF THE INVENTION

It has been discovered that "thin stillage", discharged from a centrifuge in which relatively large insoluble solids in an ethanol stillbottoms stream are separated from "whole stillage", may be further separated by an ultrafiltration (UF) membrane means without blinding the membrane, into a permeate stream in which not only essentially all the insoluble portion of the thin stillage $>0.1$ μm is removed as concentrate, but also at least 50% of solubles having a molecular weight $>2 \times 10^5$ Daltons, including dissolved proteins in the thin stillage, is removed, yet maintaining a permeate recovery of at least 50%, preferably at least 60%. In a subsequent nanofiltration (NF) second step, the UF permeate from the UF system is further separated to produce a permeate recovery of more than 70% with a rejection of less than 30% of both the lactic acid and the glycerol, preferably less than 25%. Essentially all molecules larger than lactic acid or glycerol are removed in the NF concentrate.

It has also been discovered that concentrates produced from preselected UF and NF modules in the abovedescribed two-step process, are so rich in solids, both insolubles and dissolved, that the concentrates may be dried in a drying zone rather than an evaporation zone, thus saving the costs of operating and maintaining evaporators in an existing plant, and avoiding the installation of evaporators in a new plant built to utilize the process of this invention. In the event that it is economical to use existing evaporators, the UF concentrate which has been substantially stripped of its relatively low mol wt dissolved solids, but contains essentially all 'heavies' (mol wt $>2 \times 10^5$ Daltons) in an amount from 25% to 40% by weight, may be concentrated in the evaporators prior to being dried. The much lower volume of the UF concentrate, containing the aforementioned insolubles, allows low cost operation of the evaporators. Similarly, the NF concentrate, essentially free from insolubles but containing from 10% to 30% solids having a mol wt in the range $>$ about 200 Daltons, but $<2 \times 10^5$ Daltons, the concentration depending upon how effectively these solids have been removed in the preceding UF filtration step, may also be concentrated in the evaporators prior to being dried in the dryers.

It is therefore a general object of this invention to provide a two-step filtration process for filtering the aforesaid thin stillage for the specific purpose of recovering a mixture of lactic acid and glycerol substantially free from soluble proteins in a first ultrafiltration (UF) step, with a tubular UF membrane, preferably in a cross-flow UF module; and, in a second step, to capitalize on the essentially identical mol wts of lactic acid and glycerol which allows them to be separated together in the permeate from a nanofiltration (NF) step under the prevalent pH conditions, using a NF membrane in a cross-flow spiral wound module, or, a tubular NF membrane, preferably in a cross-flow NF module, the heavier molecules being removed in the concentrate; whereby, either concentrate, or both, may be flowed directly to a drying zone including rotary driers, so as to bypass using conventional evaporators and to save the costs relating to operation thereof.

It is a specific object of this invention to provide a two-step process for recovering lactic acid and glycerol together, from thin stillage, comprising, in a first step, flowing thin stillage essentially free from insoluble suspended solids larger than about 10 μm, in cross-flow to an ultrafiltration (UF) zone, at a temperature in the range from about 30°0 C. to 100° C. and at relatively low pressure in the range from 1 atm (atmosphere) to 10 atm, preferably 1–5 atm, said UF zone having at least one module containing a UF membrane having a pore size smaller than 0.1 μm, preferably in the range from 0.005 μm–0.05 μm sufficient to remove solid particles $>0.05$ μm and 'heavies' comprising molecules in the range from 1000–200,000 Daltons; and, removing an ultrafiltered permeate (UF permeate) and an ultrafiltered concentrate (UF concentrate) with a permeate recovery of at least 50%; said UF permeate containing essentially all 'lights' comprising soluble solids having a mol wt $<200,000$ Daltons, preferably $<50,000$ Daltons which were present in the thin stillage; said UF concentrate containing essentially all solid insoluble particulates $>0.05$ μm and essentially all heavies, present in the thin stillage; and, in a second step, flowing said UF permeate at a temperature in the range from about 30°0 C.–100° C. and at relatively low pressure in the range from 5 atm to 40 atm, preferably 10–25 atm, in cross-flow, to a (NF) nanofiltration zone having a NF membrane contained in either a spiral wound or tubular cross-flow module permeable to non-ionized molecules having a mol wt smaller than about 200 Daltons, preferably smaller than 150 Daltons; and, removing a nanofiltered permeate (NF permeate) and a nanofiltered concentrate (NF concentrate) with a recovery of at least 50%; said NF permeate containing at least 70% of lactic acid and glycerol present in said UF permeate, said NF permeate being essentially free of dissolved solids and multivalent ions (and ions which contribute to hardness) having a mol wt >200 Daltons, preferably >150 Daltons; said NF concentrate containing essentially all soluble solids having a mol wt >200 Daltons, preferably >150 Daltons; and, flowing said UF concentrate and said NF concentrate to a solids-concentration zone to be further concentrated; whereby no permeate is flowed to an evaporator, and the operation and maintenance of an evaporation zone for producing syrup from microfiltered thin stillage is obviated.

It is another specific object of this invention to recover at least 70% of lactic acid and glycerol present in thin stillage, also to recover a demineralized water stream from the thin stillage, and to recycle the demineralized water to the fermentation zone, in a process comprising, flowing the NF permeate from the NF filtration zone at a temperature in the range from about 30°0 C.-100° C., preferably 30° C.-60° C., and at relatively high pressure in the range from 25 atm to 70 atm, preferably 40-60 atm, in cross-flow, to a (RO) reverse osmosis zone having a module with an RO membrane contained in either a spiral wound or tubular cross-flow module permeable to non-ionized molecules having a mol wt smaller than about 50 Daltons, preferably smaller than 20 Daltons; and, removing a RO permeate and a RO concentrate with a recovery of at least 50%; whereby the RO concentrate contains at least 90% of lactic acid and glycerol concentration present in the NF permeate, and the RO permeate is water essentially free of dissolved solids and organic compounds having a molecular weight >50; and, flowing the RO permeate to a fermentation zone or to boiler water make-up feed.

It is a specific object of this invention to operate the UF first step of the membrane separation processes as a "feed and bleed" membrane separation unit using plural cross-flow tubular membrane modules, so that the conc of solids in the concentrate (and bleed stream) is in the range from 15% to 35%, preferably from 20%-30%; to operate the NF second step with a spiral wound polymeric membrane module so that the conc of solids in the concentrate is in the range from 3% to 20%, preferably from 5%-12%; and, to operate the RO third step with a spiral wound polymeric membrane module so that the conc of solids in the concentrate is in the range from about 10-25%, and there are no solids in the permeate. The NF second step and RO third steps may also be operated in a "feed and bleed" mode.

It has also been discovered that the essentially lactic acid-free and glycerol-free concentrates from the foregoing UF and NF filtration steps, when dried to a moisture content of less than 5%, preferably less than 1%, results in a proteinaceous feed substantially free of lactic acid and glycerol, for ruminants. This feed when mixed with solids recovered from centrifuged stillbottoms, contains essentially all water-insoluble solids, all proteins (>1000 Daltons), and all fatty acids (>150 Daltons) in the whole stillage. An alternative proteinaceous feed for fish which do not benefit from the lactic acid and glycerol, is not mixed with solids recovered from centrifuged stillbottoms, and contains water-insoluble solids having a primary particle size in the size range from 0.005 μm-0.10 μm, proteins having a mol wt >1000 Daltons, and fatty acids having a mol wt >150 Daltons.

It is a further specific object of this invention to separate lactic acid and glycerol, together, having a combined concentration in the range from 10 to 25% by wt in a concentrate discharged from a spiral wound RO membrane from which a permeate of RO water essentially free of ions is recycled to the fermenter.

The term "essentially all" as used herein refers to at least 95% by wt, preferably more than 97% by wt, and most preferably more than 99% by wt; and the term "essentially free" refers to less than 5% by wt, preferably less than 3% by wt, and most preferably less than 1% by wt.

BRIEF DESCRIPTION OF THE DRAWINGS

The foregoing and additional objects and advantages of the invention will best be understood by reference to the following detailed description, accompanied with schematic illustrations of preferred embodiments of the invention, in which illustrations, like reference numerals refer to like streams, processing zones, or processing steps, and in which.

DETAILED DESCRIPTION OF PREFERRED EMBODIMENTS

Figure 1:
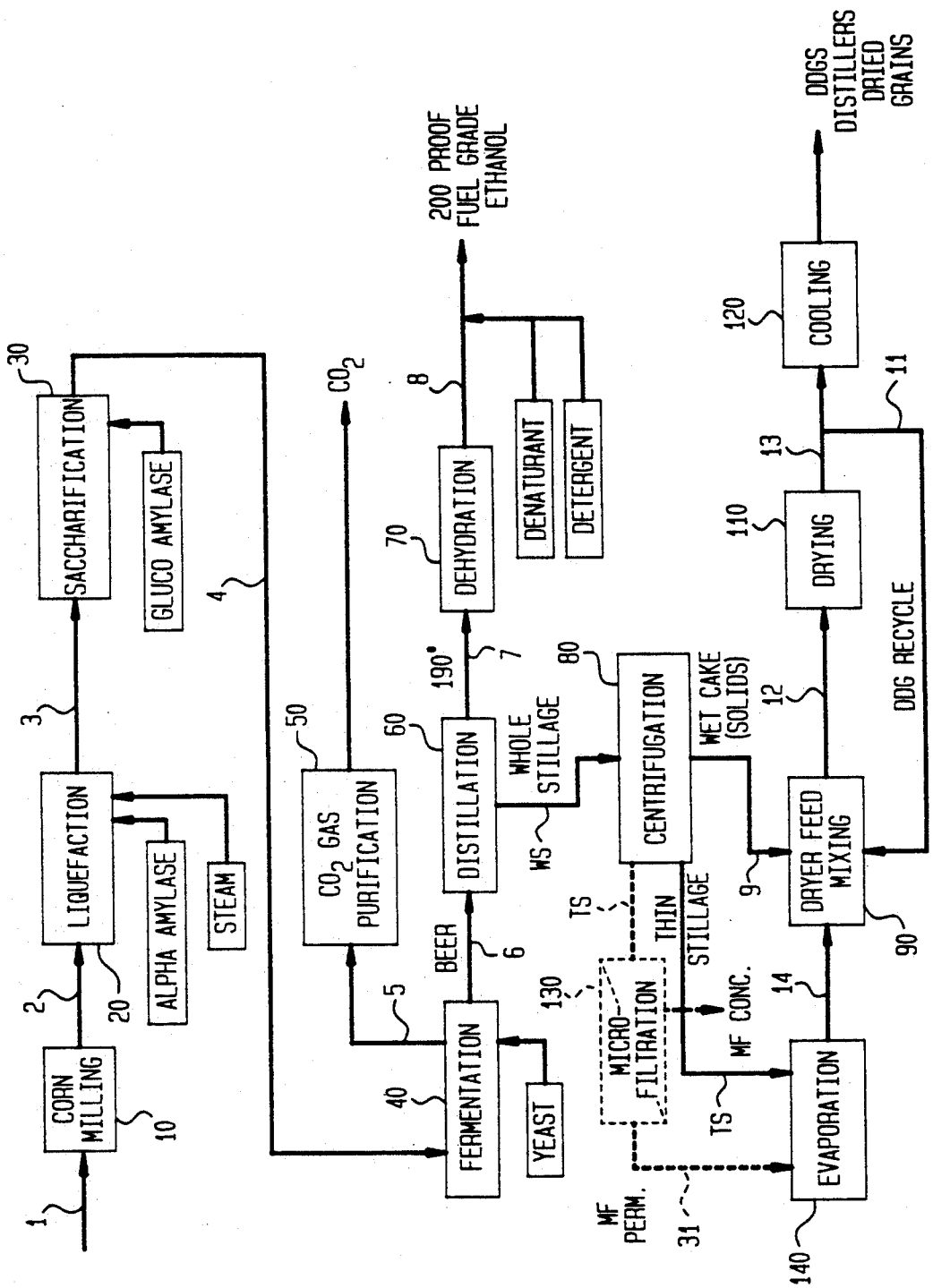
FIG. 1 is a simplified flow diagram schematically illustrating the prior art semi-continuous process for the production of industrial ethanol based on the dry-milling of corn, in which process various zones are identified by the unit operation therein; and, in phantom outline, a prior art microfiltration step for clarifying thin stillage to produce a filtrate which is concentrated to syrup.

The overall process for the dry milling of corn for the production of industrial ethanol by fermentation is schematically illustrated in simplified form in FIG. 1 in which each unit operation preceding distillation is a batch operation. Feed corn introduced at 1 is milled in a corn milling zone 10 where the corn is pulverized to a powdery mass of "corn meal" which is discharged at 2 into a liquefaction zone 20. Steam and alpha amylase are also introduced into zone 20 to produce a "corn slurry" which is cooked before it is discharged at 3 into a saccharification zone 30 into which gluco amylase is introduced to convert the corn to sugar. A sugary mass of "corn mash" 4 is discharged into fermentation zone 40 which is inoculated with yeast selected to produce a high yield of ethanol, in the concentration range from 8% to about 12%, in the presence of lactic acid and glycerol.

Carbon dioxide gas produced during fermentation is discharged at 5 and is flowed to a $CO_2$ gas purification zone 50 in which the gas is purified prior to being sold. Upon completion of the fermentation reaction a beer 6 is discharged to an ethanol distillation zone 60 including an ethanol column, and, an azeotropic distillation column, from which wet ethanol 7 is flowed to a dehydration zone 70. Upon dehydration the dried ethanol 8 is "doctored" with denaturant and detergent before it is sold.

Whole stillage bottoms from the ethanol column in the distillation zone 60 is discharged at WS to a centrifugation zone 80 from which a wet cake 9 is discharged to a dryer feed mixing zone 90 in which a DDG recycle stream 11 is mixed with the wet cake. The mixed wet cake 9 and DDG recycle 11 is discharged at 12 to a drying zone 110 including plural rotary dryers. A portion of the dried solids 13 from the drying zone 110 is recycled as the DDG recycle 11. Dried solids 13 are cooled in cooling zone 120 before being shipped as distillers dried grains (DDGS).

The thin stillage liquid discharge TS of a centrifuge is led to an evaporation zone 140 where it is concentrated to a syrup 14 which is mixed with wet cake 9 from the centrifuge before the mixture is dried in drying zone 110.

The conc of solids in thin stillage TS was decreased by removing solids $>0.2$ μm in the prior art microfiltration zone 130 shown in phantom outline. The microfiltrate 31 was flowed to the evaporator to form a syrup 16, used as described before.

Figure 2:
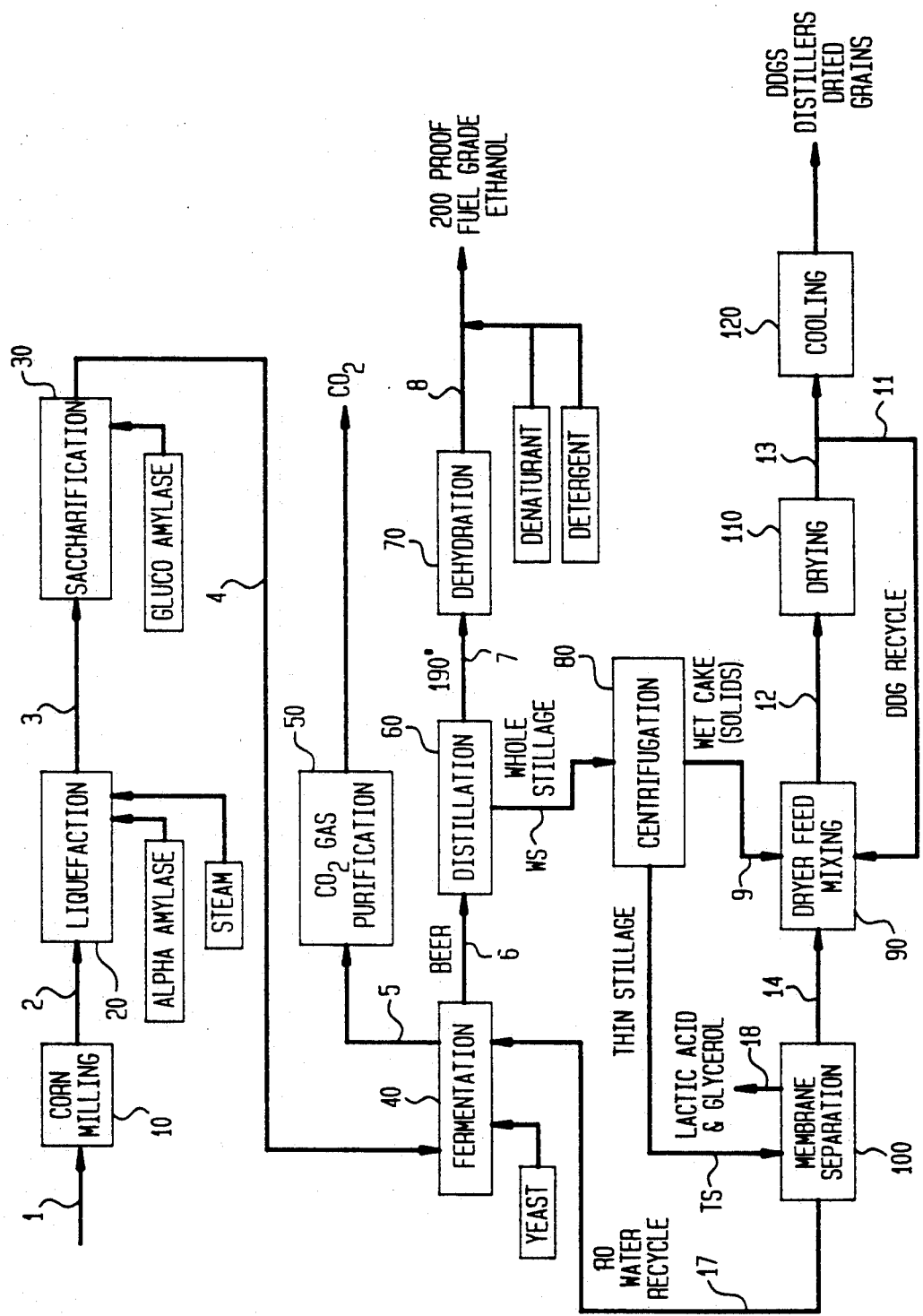
FIG. 2 is a simplified flow diagram schematically illustrating the substitution of a membrane separation zone for the evaporators in the prior art process shown in FIG. 1.

Referring now to FIG. 2, there is shown the overall process flowsheet for the novel process in which membrane separation zone 100 comprising the membrane filtration processes described hereinabove, are carried out. As illustrated, membrane separation zone 100 is substituted for the evaporation zone of the prior art process. Thin stillage TS is flowed to the membrane separation zone 100 and demineralized (RO) water 17, recovered from the thin stillage is recycled to the fermentation zone 40. Lactic acid and glycerol 18 are recovered together from the thin stillage. If separation of the lactic acid from the glycerol is desired, the mixture 18 is led to a liquid-liquid extraction unit or other suitable unit operation (not shown) which is operated under conditions effective to make the separation desired. Details of the membrane separation zone 100 are schematically illustrated in FIG. 3.

Thin stillage has a pH in the range from 3 to 5 and contains from about 5-15% total solids, typically 6-12% by wt. From about 3 to 7% by wt are soluble solids, the remaining being insoluble. The analysis of the solids which include lactic acid and glycerol is as follows:

|  | Range |
| --- | --- |
| Total proteins | 0.7 to 2.5% by wt |
| Total fats | 0.3 to 2.0% by wt |
| Lactic acid | 0.5 to 2.5% by wt |
| Glycerol | 0.5 to 2% by wt |

Figure 3:
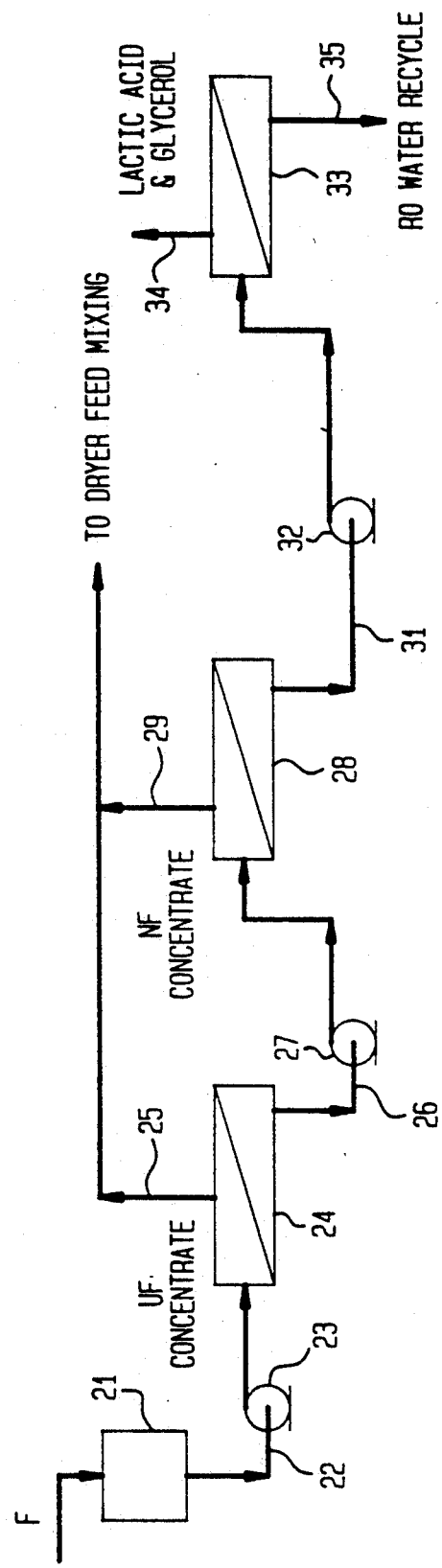
FIG. 3 is a simplified schematic flow diagram of a membrane separation zone in which step-wise membrane separations of thin stillage are continuously effected with successively more restrictive membranes, each with a permeate recovery of at least 50%. In a specific embodiment of the separation process illustrated, the UF membrane means comprises two modules connected in series, each housing tubular membranes and operated in a cross-flow mode to avoid blinding the membranes. The NF and RO modules in the membrane separation zone are spiral-wound polymeric membranes which are more economical than tubular membranes. Each step of the membrane separation process is operable for a period of time sufficient to allow the substitution of a membrane separation zone for a conventional evaporation zone in a commercial facility.

Referring to FIG. 3 there is illustrated a continuous step-wise membrane separation process in which thin stillage feed F is held in a feed tank 21 from which a stream 22 is pumped through pump 23 to UF membrane means 24. Typically the UF means comprises plural UF modules through which stream 22 is pumped in series, in a cross-flow mode, that is, the stream 22 is flowed through tubular membranes so that permeate leaves the a shell-and-tube type module through the walls of the tubes in a direction substantially orthogonal to the direction of flow of the thin stillage through the tubes. Alternatively, the thin stillage may be flowed through the shell side so that permeate leaves through the tubes and concentrate leaves through the shell side.

As indicated, the thin stillage F is flowed through the tube side of the UF means 24. UF concentrate 25 is discharged to dryer feed mixing zone 90 (shown in FIG. 2). UF permeate 26 is pumped by pump 27 to a NF membrane means 28 containing plural NF modules with spiral-wound semipermeable membranes, from which a NF concentrate 29 is discharged to dryer feed mixing zone 90.

NF permeate 31 is pumped by high pressure pump 32 to RO module means 33 containing plural RO modules with spiral-wound RO membranes from which RO concentrate 34 is discharged containing a major proportion, preferably at least 70%, and most preferably essentially all, the lactic acid and glycerol in stream 16. RO permeate 35 is essentially pure water which may be used as boiler feed, or, more preferably recycled to the fermenter in the fermentation zone 40 (shown in FIGS. 1 & 2).

It is preferred that each membrane means 24, 28 and 33 be operated in the "feed and bleed" mode to improve recovery. In such an operation, a large stream of concentrate, from 2 to 20 times larger than the flow rate to the module, is recirculated by a recirculation pump. Since the "head" on the recycle pump is determined mainly by the losses due to pressure drop through the module, operation of such a system allows a very high mass flow through the module at the elevated pressure (supplied by the feed pump for that module) at relatively small cost.

The following mass balance for lactic acid and glycerol through the membrane separation means is for a typical thin stillage flow rate of 900 gal/min in which the total conc of lactic acid and glycerol is less than 3% w/w:

TABLE 1

| Stream Identif. | 16 | 19 | 21 | 24 | 25 | 28 | 29 |
| --- | --- | --- | --- | --- | --- | --- | --- |
| Flow rate, gpm | 900 | 180 | 720 | 180 | 540 | 54 | 486 |
| Lactic acid, % w/w | 1.7 | 1.7 | 1.7 | 2.5 | 1.4 | 14.0 | <0.1 |
| Glycerol, % w/w | 1.1 | 1.2 | 1.0 | 1.0 | 1.0 | 9.8 | <0.1 |

The foregoing mass balance is not based on a diafiltration option for improved recovery of lactic acid and glycerol to enhance the yield in the UF and NF filtration steps. In the diafiltration option, the recycle stream used in a "feed-and-bleed" mode is diluted with RO water. When the diluted recycle is pumped through the module the yield of lactic acid and glycerol is enhanced. Such diafiltration may be practiced in any manner known in the art, the goal being to recycle diluted concentrate at relatively low cost to enhance yield of product.

In the UF membrane means, a channel which is too narrow will be plugged. It is most preferred to use a UF membrane with a 4 mm or 6 mm channel. UF membranes which have a pore size of $<0.05$ μm and provide good service are as follows:

| | |
| --- | --- |
| Ceramem PMA-0050-P-4 mm | Alcoa 19P19-40-500 Å |
| Ceramem PMA-0010-P-4 mm | Alcoa 19P19-60-500 Å |

-continued

| Ceramem PMA-0005-P-4 mm | Alcoa 19P19-40-100 Å |
| Alcoa 19P19-60-100 Å | Alcoa 19P19-40-50 Å |
| Alcoa 19P19-60-50 Å and | Millipore ceramic <500 Å |

The following NF membranes provide good service:
Filmtec NF40; Filmtec XP-45;
Desal 5 and Hydranautics PVD1.

The following RO membranes provide good service:
Filmtec BW-30; Filmtec SW-30; Filmtec SW-30HR UOP RO membrane Desal RO membrane Osmonics RO membrane Nitto RO membrane.

Though membranes having a channel smaller than 4 mm are more economical to use, their use incurs a higher risk of pluggage. To take advantage of the economics of using membranes with a 2 mm channel (say), it is desirable to prefilter the thin stillage using a microfiltration membrane having a pore size of about 1 μm. Of course a smaller pore size may be used, as was reported by Burris, supra, but whichever MF membrane is used, the MF permeate will be flowed to the membrane separation zone 100, and the MF concentrate flowed to the dryer feed mixing zone 90, or the drying zone 110. The use of the evaporation zone 140 (see FIG. 1) is avoided.

It will also be appreciated that the permeate recovery obtained through each membrane zone will depend upon the amount of concentrate recycled, and whether the zone is operated in a diafiltration mode. Since the overall recovery of NF permeate is desirably about 80% it will be appreciated that operation of the membrane modules without recycling concentrate is not practical. The same consideration applies to recovery of RO water.

Having thus provided a general discussion of the problems which have been addressed by the process of this invention, a detailed description of preferred embodiments of the invention, and the unexpected manner in which the problem was solved by utilizing particular modes of operation of various membrane means, it is to be recognized that the scope of this invention not be limited to a slavish duplication of the specific preferred embodiments and illustrations provided, but to the scope of the appended claims.

We claim:

1. A two-step membrane recovery process for recovering lactic acid and glycerol, together, from thin stillage obtained from the distillation of beer produced in a fermentation zone, said process comprising,
   (1) in a first membrane recovery step,
      (a) flowing said thin stillage essentially free from insoluble suspended solids larger than about 10 μm, in cross-flow, to an ultrafiltration (UF) zone, at a temperature in the range from about 30°0 C.-100° C. and at a pressure in the range from 1 atm to 10 atm, said UF zone having at least one module containing a UF membrane having a pore size smaller than 0.1 μm, sufficient to remove suspended solids >0.1 μm and 'heavies' in the range from 1000-200,000 Daltons; and,
      (b) withdrawing an ultrafiltered permeate (UF permeate) and an ultrafiltered concentrate (UF concentrate) from said UF zone with recovery of UF permeate being at least 50% in said UF zone; said UF permeate containing essentially all 'lights' consisting of soluble solids having a molecular weight <1000 Daltons, said solids being present in said thin stillage; said UF concentrate containing essentially all solid insoluble particulates >0.1 μm and essentially all 'heavies' consisting of soluble solids having a molecular weight >1000 Daltons; and,
   (2) in a second membrane recovery step,
      (a) flowing said UF permeate at a temperature in the range from 30°0 C.-100° C. and at a pressure in the range from 5 atm to 40 atm, in cross-flow, to a nanofiltration (NF) zone having at least one module with a NF membrane permeable to non-ionized molecules having a molecular weight <200 Daltons; and,
      (b) withdrawing a nanofiltered permeate (NF permeate) and a nanofiltered concentrate (NF concentrate) from said NF zone with recovery of NF permeate being at least 50% in said NF zone; said NF permeate containing a major proportion by weight of lactic acid and glycerol present in said UF permeate, said NF permeate being essentially free of dissolved solids having a molecular weight >200 Daltons; said NF concentrate containing essentially all soluble solids having a molecular weight >200 Daltons; and,
   (3) recovering said UF concentrate and said NF concentrate; whereby no UF permeate or NF permeate is flowed to an evaporation zone, and the operation and maintenance of an evaporator for producing syrup from thin stillage is obviated.

2. The process of claim 1 wherein said pore size of said UF membrane is no greater than 0.05 μm so as to remove suspended insoluble solid particles >0.05 μm; said thin stillage to said UF zone is at a pressure in the range from 1-5 atm; said NF membrane in said NF zone is permeable to molecules <150 Daltons; said UF permeate to said NF zone is at a pressure in the range from 10-25 atm; said NF permeate contains at least 70% by weight of said lactic acid and glycerol present in said UF permeate; and said UF concentrate and NF concentrate are recovered by flowing to a solids-concentration zone.

3. The process of claim 1, including a third membrane recovery step, comprising,
   (a) flowing said NF permeate at a temperature in the range from about 30°0 C.-60° C. and at a pressure in the range from 25 atm to 70 atm, to a reverse osmosis (RO) zone containing at least one RO membrane permeable to molecules having a molecular weight <50 Daltons; and,
   (b) withdrawing a RO permeate and a RO concentrate with recovery of said RO permeate being at least 50% in said RO zone;
   whereby said RO concentrate contains about 90% of lactic acid and glycerol present in said NF permeate, and said RO permeate is demineralized water essentially free of dissolved solids; and,
   recirculating said RO permeate for reuse.

4. In a process for the production of industrial ethanol by dry-milling corn, fermenting a saccharified corn meal in a fermentation zone to produce a beer, distilling said beer to produce said ethanol and whole stillage, and centrifuging said whole stillage to obtain a separation of wet cake and thin stillage containing lactic acid and glycerol, the improvement comprising,
   flowing said thin stillage to a membrane separation zone comprising at least two filtration zones, an ultrafiltration (UF) zone and a nanofiltration (NF)

zone, each zone providing a permeate recovery of at least 50%, including, flowing said thin stillage to said UF zone provided with a UF membrane having a sufficiently small pore size to reject a major portion by weight of dissolved solids having a molecular weight $>2\times10^5$ Daltons and essentially all suspended solids $>0.05$ $\mu$m, so as to obtain an ultrafiltered permeate (UF permeate) essentially free of suspended solids $>0.05$ $\mu$m, and an ultrafiltered concentrate (UF concentrate) containing solids having a nominal diameter $>0.05$ $\mu$m;

flowing said UF permeate to said NF zone provided with a semipermeable membrane effective to reject dissolved solids having a molecular weight $>200$ Daltons in a nanofiltered concentrate (NF concentrate);

recovering a nanofiltered permeate (NF permeate) containing a major portion by weight of said lactic acid and glycerol present in said thin stillage; and, recovering said UF concentrate and said NF concentrate.

5. The process of claim 4 comprising, in addition, flowing said UF concentrate and said NF concentrate to a drying zone; and, drying said UF and NF concentrates to a moisture content less than 5%.

6. The process of claim 4 comprising, in addition, (a) flowing said NF permeate at a temperature in the range from 30°0 C.–60° C. and at a pressure in the range from 25 atm to 70 atm, to a reverse osmosis (RO) zone containing a RO membrane permeable to molecules having a molecular weight $<50$ Daltons;

(b) withdrawing a RO permeate and a RO concentrate with recovery of said RO permeate being at least 50% through said RO zone; whereby said RO concentrate contains at least 90% of lactic acid and glycerol present in said NF permeate, and said RO permeate is water essentially free of dissolved solids; and, (c) flowing said RO permeate for reuse.

7. The process of claim 6 wherein said UF membrane is an inorganic tubular membrane; said NF membrane is an organic membrane of spiral wound material; said NF permeate is flowed to said RO zone at a pressure in the range from 40–60 atm; said RO membrane is an organic membrane of spiral wound material; and, recovery of RO water is about 90%.

8. The process of claim 6, comprising flowing said RO water to said fermentation zone.

9. A proteinaceous animal feed obtained from corn thin stillage having a pH in the range from 3 to 5 and containing from 5 to 15% total solids, said thin stillage in turn being obtained from whole stillage after fermentation of beer, said feed being essentially free from lactic acid and glycerol, other organic components of said thin stillage being maintained in said feed having a moisture content of less than 5%, said feed consisting essentially of (i) water-insoluble solids having a primary particle size in the range from $>0.005$ $\mu$m to $<0.1$ $\mu$m, (ii) proteins having a molecular weight $>1000$ Daltons, and (iii) fatty acids having a molecular weight $>150$ Daltons, wherein each said (i), (ii) and (iii) is present in said corn thin stillage.

10. In a system for producing ethanol from corn, said system including, milling means for milling corn, liquefaction means for liquefying corn meal, saccharification means for saccharifying liquefied corn meal, fermentation means for fermenting saccharified corn meal, distillation means for distilling beer, and centrifuge means for centrifuging stillbottoms to provide corn thin stillage, the improvement comprising, plural membrane separation means, including, ultrafiltration (UF) membrane means in flow communication with said centrifuge means so as to receive thin stillage under sufficient pressure to produce a UF concentrate and a UF permeate, said UF membrane means including at least one tubular UF membrane having a pore size sufficient to remove molecules in the range from 1000–200,000 Daltons; and, nanofiltration (NF) membrane means in flow communication with said UF membrane means so as to receive said UF permeate under sufficient pressure to produce a NF concentrate and a NF permeate, said NF membrane means including a semipermeable membrane which effectively rejects molecules having a molecular weight $>200$ Daltons;

whereby said NF permeate contains at least 90% of lactic acid and glycerol present in said UF permeate.

11. The system of claim 10 wherein said plural membrane separation means includes, in addition, reverse osmosis (RO) membrane means in flow communication with said NF membrane means so as to receive said NF permeate under sufficient pressure to produce a RO concentrate and a RO permeate, said RO membrane means including a semipermeable membrane which effectively rejects molecules having a molecular weight $>150$ Daltons;

whereby said RO permeate is demineralized water containing essentially no lactic acid or glycerol.

12. A proteinaceous animal feed obtained from corn thin stillage having a pH in the range from 3 to 5 and containing from 5 to 15% total solids, said thin stillage in turn being obtained from whole stillage after fermentation of beer, said feed being produced in a process for the production of industrial ethanol by dry-milling corn, comprising, fermenting a saccharified corn meal in a fermentation zone to produce a beer, distilling said beer to produce said ethanol and whole stillage, and centrifuging said whole stillage to obtain a separation of wet cake and thin stillage containing lactic acid and glycerol, flowing said thin stillage to a membrane separation zone comprising at least two filtration zones, an ultrafiltration (UF) zone and a nanofiltration (NF) zone, each zone providing a permeate recovery of at least 50%, said UF zone having a UF membrane with a sufficiently small pore size to reject a major portion by weight of dissolved solids having a molecular weight $>2\times10^5$ Daltons and essentially all suspended solids $>0.05$ $\mu$m, so as to obtain an ultrafiltered permeate (UF permeate) essentially free of suspended solids $>0.05$ $\mu$m, and an ultrafiltered concentrate (UF concentrate) containing solids having a nominal diameter $>0.05$ $\mu$m;

flowing said UF permeate to said NF zone having a semipermeable membrane effective to reject dissolved solids having a molecular weight $>200$ Daltons in a nanofiltered concentrate (NF concentrate);

recovering a nanofiltered permeate (NF permeate) containing a major portion by weight of said lactic acid and glycerol present in said thin stillage;

recovering said UF concentrate and said NF concentrate;

flowing said UF concentrate and said NF concentrate to a drying zone; and, drying said UF and NF concentrates to a moisture content less than 5%.

* * * * *